(12) United States Patent
Sommers et al.

(10) Patent No.: US 7,217,126 B2
(45) Date of Patent: May 15, 2007

(54) DENTAL INSTRUMENT SHARPENING STONE SYSTEM

(76) Inventors: Corey Sommers, 2400 W. El Camino Real #1119, Mountain View, CA (US) 94040; Mimi Sommers, 2400 W. El Camino Real #1119, Mountain View, CA (US) 94040; Randal B. Chinnock, 53 McGilpin Rd., Sturbridge, MA (US) 01566; Jeffrey S. Melanson, 90 Flake Hill Rd., Sturbridge, MA (US) 01566

( * ) Notice: Subject to any disclaimer, the term of this patent is extended or adjusted under 35 U.S.C. 154(b) by 0 days.

(21) Appl. No.: 11/220,151

(22) Filed: Sep. 6, 2005

(65) Prior Publication Data

US 2006/0009140 A1 Jan. 12, 2006

Related U.S. Application Data

(62) Division of application No. 10/391,354, filed on Mar. 18, 2003, now abandoned.

(51) Int. Cl.
*A61C 1/00* (2006.01)
(52) U.S. Cl. ...................................... 433/31
(58) Field of Classification Search .............. 433/30, 433/31, 141, 142, 143, 144, 147; 7/120, 7/170; 451/45, 423, 461, 552
See application file for complete search history.

(56) References Cited

U.S. PATENT DOCUMENTS

| | | | | |
|---|---|---|---|---|
| 881,691 | A | * | 3/1908 | Hughes ...................... 433/134 |
| 1,898,422 | A | * | 2/1933 | Champlin ...................... 7/120 |
| 2,469,586 | A | * | 5/1949 | Wallace ...................... 451/507 |
| 3,722,146 | A | * | 3/1973 | Rodriguez et al. .......... 451/180 |
| 3,812,626 | A | * | 5/1974 | Thompson ................... 451/358 |
| 3,986,302 | A | * | 10/1976 | Biardi ........................ 451/342 |
| 4,182,037 | A | * | 1/1980 | Ellman et al. .............. 433/110 |
| 6,782,576 | B1 | * | 8/2004 | Valencic et al. ............... 7/158 |

FOREIGN PATENT DOCUMENTS

GB 553369 A * 5/1943

* cited by examiner

*Primary Examiner*—Todd E. Manahan
(74) *Attorney, Agent, or Firm*—Brian M. Dingman, Esq.; Mirick, O'Connell, DeMallie & Lougee, LLP

(57) ABSTRACT

A hand-held dental mirror carrying a sharpening stone for a dental instrument such as a curette, comprising a shaft supporting a mirror, a hand grip coupled to the shaft, and a sharpening stone coupled to the shaft.

8 Claims, 6 Drawing Sheets

DENTAL INSTRUMENT SHARPENING STONE SYSTEM

CROSS REFERENCE TO RELATED APPLICATION

This application is a Divisional application of application Ser. No. 10/391,354, filed on Mar. 18, 2003, now abandoned. Priority is claimed.

FIELD OF THE INVENTION

This invention relates to a dental instrument that carries a dental instrument sharpening stone.

BACKGROUND OF THE INVENTION

Sharp dental instruments called curettes (alternate spelling: curets) are used during the scaling or planing of human teeth during hygienic cleaning. These curettes are typically made of stainless steel and require frequent resharpening. This is typically done on a conventional sharpening stone. Such stones may be rectangular slabs or wedges. They may have rounded edges or be straight or tapered cylinders for the sharpening of interior radii. Kits with a variety of stone shapes are sold. The flat surface of the stone may also contain V-grooves for the simultaneous sharpening of two cutting edges. Many types of fixtures have been developed to achieve a more consistent finish when performing manual sharpening. Many other powered sharpening systems have also been developed.

To prevent cross-contamination of patients, all dental instruments are sterilized between patients by steam autoclave (generally the only sterilization means available in a dental office). The powered sharpening systems are not sterilizable. Therefore, after sharpening, the curette must be resterilized. Since this takes at least 10–20 minutes, the powered sharpening systems may only be used between patients, not during treatment of a patient. This also applies to many of the manual sharpening systems.

In contrast, hand-held sharpening stones are typically sterilizable. If they are sterile, this means they may be used before or after the curette is sterilized. This allows resharpening of the curette either before a patient, or during a treatment when the curette becomes dull. However, when scaling, the hygienist or dentist (hereinafter, "hygienist") generally holds a dental mirror in one hand and the curette in the other. Sharpening a curette with a hand-held stone requires the hygienist to free their other hand. The hygienist must also turn away from the patient to retrieve the stone from the instrument tray, and then replace it after the sharpening. These steps waste time and motion, and inhibit the user from sharpening their tools at the optimum intervals. Working with dull tools increases treatment time, contributes to hygienist fatigue, results in inferior cleaning of the teeth, and may increase the risk of unintended damage to the mouth due to greater forces required for difficult planing.

SUMMARY OF THE INVENTION

The invention solves the problem of sharpening efficiency during a patient procedure by combining the sharpening stone with another dental instrument, preferably the dental mirror. The invention allows the hygienist to very quickly resharpen the curette during a procedure. To resharpen the curette, the mirror and curette are withdrawn from the mouth. How each tool is gripped might then have to be adjusted depending on how the tools are held during use, and depending on the preferred sharpening technique. This is a matter of user choice. The curette tip is then drawn along the sharpening stone in a way that maintains perpendicularity between the cutting surface and the stone. Just a few strokes of the curette edges along the stone is typically sufficient to restore sharpness.

Several embodiments of the invention have several components in common: mirror, mirror holder, shaft, grip, sharpening stone, and stone retainer. In these embodiments, the grips and stones slide over the shaft and are locked in place by the retainer. This approach allows the interchangeability of grips and stones. Grips and stones may be easily replaced when worn, or different grips or stones may be substituted for different tasks, or if preferences change. The shaft may incorporate anti-rotation features such as a friction element (e.g., elastomer o-ring or washer), flats, grooves, or keys that prevent rotation of the stone and/or grip relative to the mirror. Stones may have a variety of profiles, such as full-round, half-round, oval, elliptical, triangular, triangular with rounded edges, and triangular with half-round. Each stone shape could also be offered in tapered versions, different grits, and different colors. Grooves may be incorporated into the stones to allow the simultaneous sharpening of both sides of the curette's tip.

This invention features a hand-held dental mirror carrying a sharpening stone for a dental instrument such as a curette, comprising a shaft supporting a mirror, a hand grip coupled to the shaft, and an instrument sharpening stone coupled to the shaft. In one embodiment, the stone is releasably coupled to the shaft. Alternatively, the stone can be a non-replaceable, permanent feature of the inventive dental instrument.

The sharpening stone may define a longitudinal opening through which the shaft passes. The means for releasably maintaining the stone coupled to the shaft may comprise a mechanical device that may be releasably coupled to the end of the shaft opposite the mirror. The hand grip and the sharpening stone may both be releasably coupled to the shaft.

Also featured is a hand-held dental instrument, carrying a sharpening stone for another dental instrument, in which the instrument includes a shaft, comprising a sharpening stone coupled to the shaft, and means for releasably maintaining the stone coupled to the shaft.

Further featured is a dental instrument sharpening stone system, in which the sharpening stone is adapted to be releasably coupled to a dental instrument which includes a shaft, comprising an elongated, integral sharpening stone body defining a longitudinal opening sized to pass the instrument shaft therethrough, and a mechanical device for releasably holding the stone body on the shaft. In this sharpening stone system, the stone body may further define a grip for the dental instrument. The stone body may have a particular cross-sectional shape adapted for sharpening a particular type of dental instrument. The sharpening stone system may further comprise an elongated grip for the instrument that defines a longitudinal opening sized to pass the instrument shaft therethrough. This stone body may be closer to the end of the shaft than is the grip. An elastic element may be located between the two to help absorb stress, particularly the stresses associated with differential thermal expansion relating to the steam autoclaving sterilization process.

BRIEF DESCRIPTION OF THE DRAWINGS

Other objects, features and advantages will occur to those skilled in the art from the following description of the preferred embodiments and the accompanying drawings, in which.

DETAILED DESCRIPTION OF THE PREFERRED EMBODIMENTS

This invention is preferably accomplished in a dental instrument such as a dental mirror that incorporates a sharpening stone for another dental instrument such as a curette. If the sharpening stone is incorporated into an instrument that is used by the hygienist at the same time as the instrument that may need sharpening (in the example given here, a curette and a dental mirror), this invention allows the user to sharpen the instrument during a patient procedure, without the need to put down or pick up anything, which results in less disruption and delay, and obviates any need for sterilization during a procedure. Preferably, the inventive dental instrument is adapted to removeably carry the sharpening stone, to allow replacement of the stone with another stone having a similar (or different) cross-sectional shape.

Figure 1:
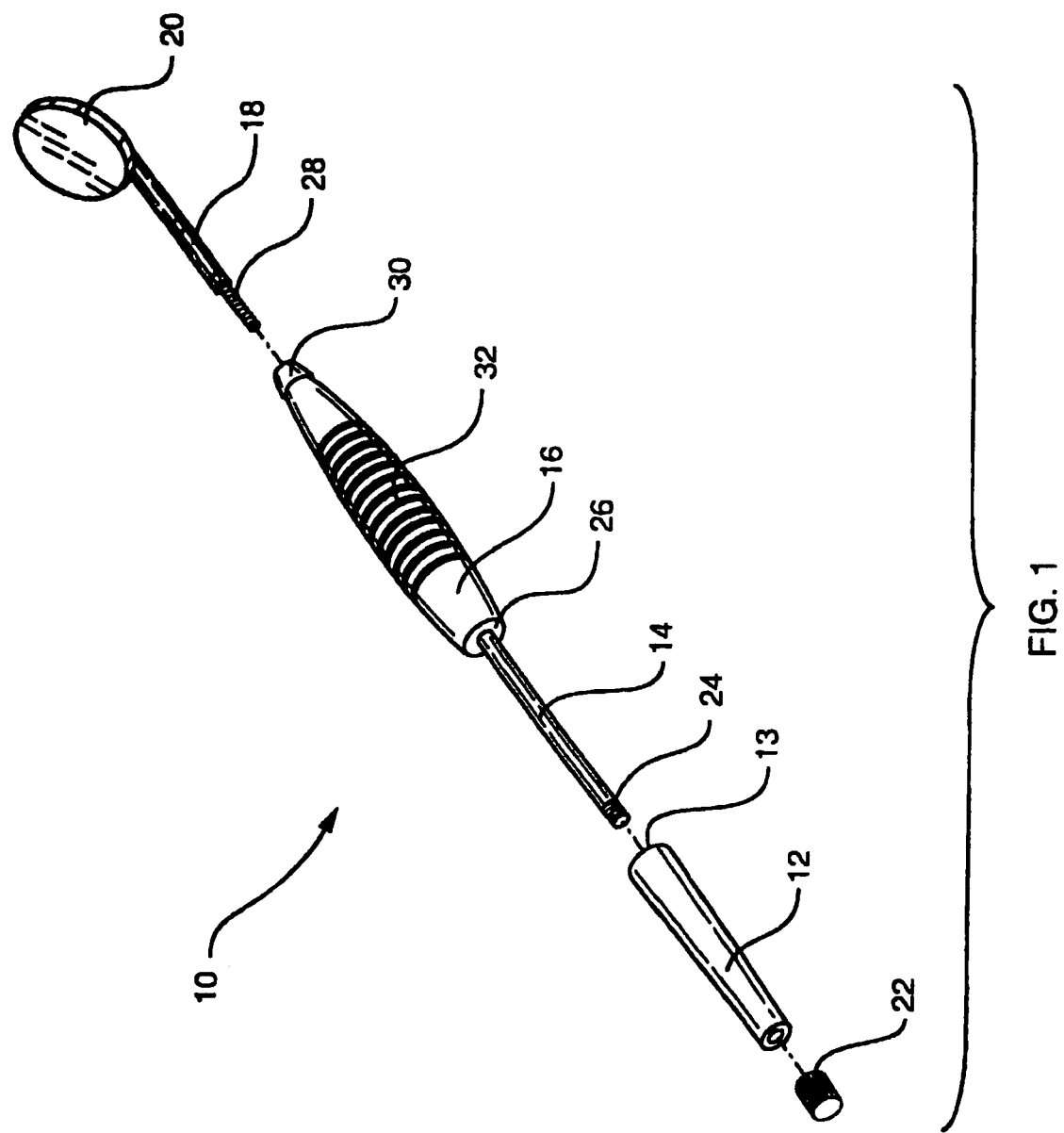
FIG. 1 is a disassembled view of one preferred embodiment of the combined dental instrument and dental instrument sharpener of this invention.
Figure 2:
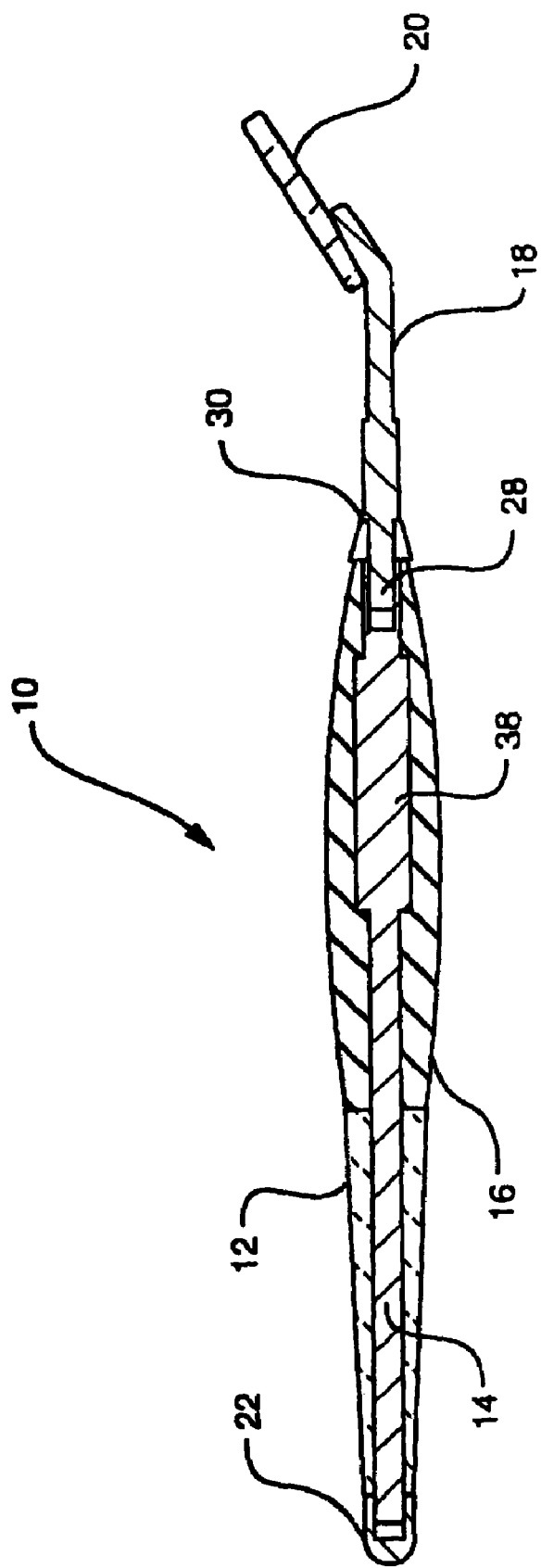
FIG. 2 is a cross-sectional view of the assembled instrument shown in FIG. 1.

There is shown in FIGS. 1 and 2 combined dental instrument and dental instrument sharpener 10 according to this invention. Instrument 10 is adapted to carry at least a sharpening stone that can be used by the hygienist to sharpen an instrument such as a curette during a dental procedure. Preferably, the stone is removable, so that it can be replaced when it is worn, or to provide a different stone for a different sharpening purpose.

Instrument 10 comprises sharpening stone 12 that has a longitudinal opening that is received on shaft 14 and held tightly in place on shaft 14 by use of knurled retaining knob 22 that is received by threaded rod end 24. The length of stone 12 is selected so that when end 13 sits against end 26 of grip 16, retainer 22 presses against end 15 of stone 12.

Grip 16 is also mounted in a similar manner to shaft 14, and sits up against retaining bull-nose end 30 of shaft 14. This arrangement allows both the sharpening stone and grip to be replaced as desired. As described above, anti-rotation features, such as key portion 38 of shaft 14, may be included to prevent rotation of the grip and/or stone.

Another optional feature of this invention is replaceable mirror portion 17 that comprises mirror support shaft 18 having mirror 20 coupled to one end, with threaded portion 28 at the other end that is received by threading in or proximate end portion 30 of shaft 14.

The modular nature of embodiment 10 is not a limitation of the invention. However, this allows the instrument to be altered and customized as desired.

Figure 3:
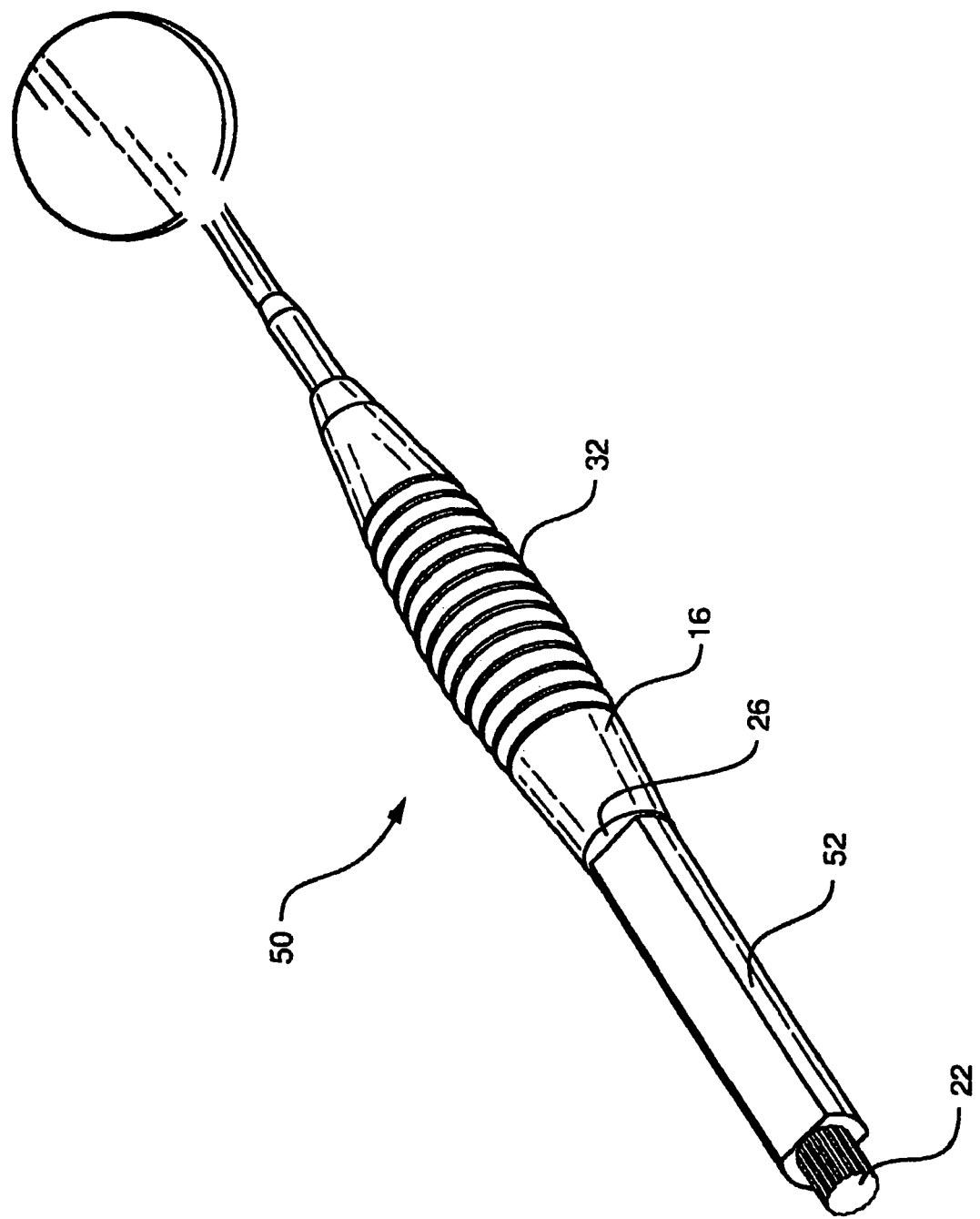
FIG. 3 is a view of an alternative embodiment of the invention.
Figure 4:
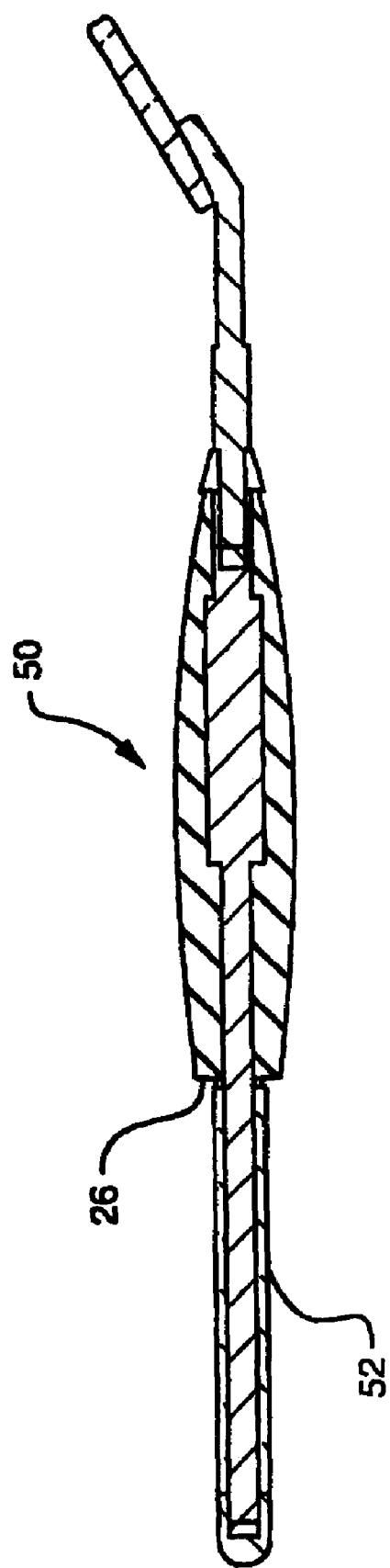
FIG. 4 is a cross-sectional view of the embodiment of FIG. 3.

FIGS. 3 and 4 show second embodiment 50. This shows in a bit more detail the radial grooves 32 in grip 16 that are an alternative feature of this invention. Also shown is a different stone shape 52 that has two flat sides and two rounded sides.

Figure 5:
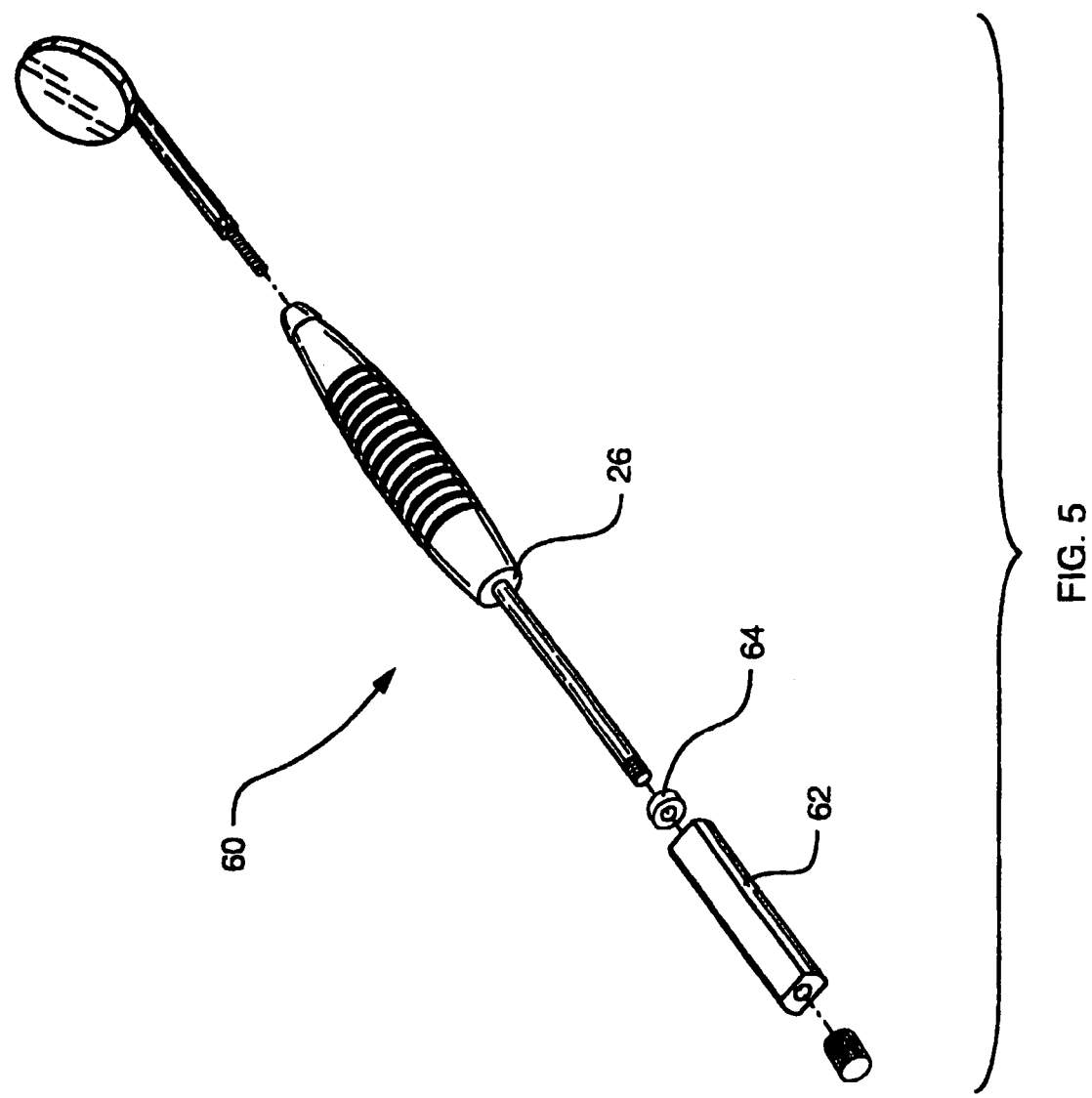
FIG. 5 is a view similar to FIG. 1 of another alternative embodiment of the invention.

FIG. 5 shows similar embodiment 60 with stone 62 and washer 64. Washer 64 provides an elastic buffer between the stone and the handle. This provides a cushion to absorb stresses caused by differences in thermal expansion of the stone and the shaft when exposed to the high temperatures of steam autoclaving. The soft washer may also serve as a friction element to prevent inadvertent rotation of the stone relative to the grip.

Figure 6:
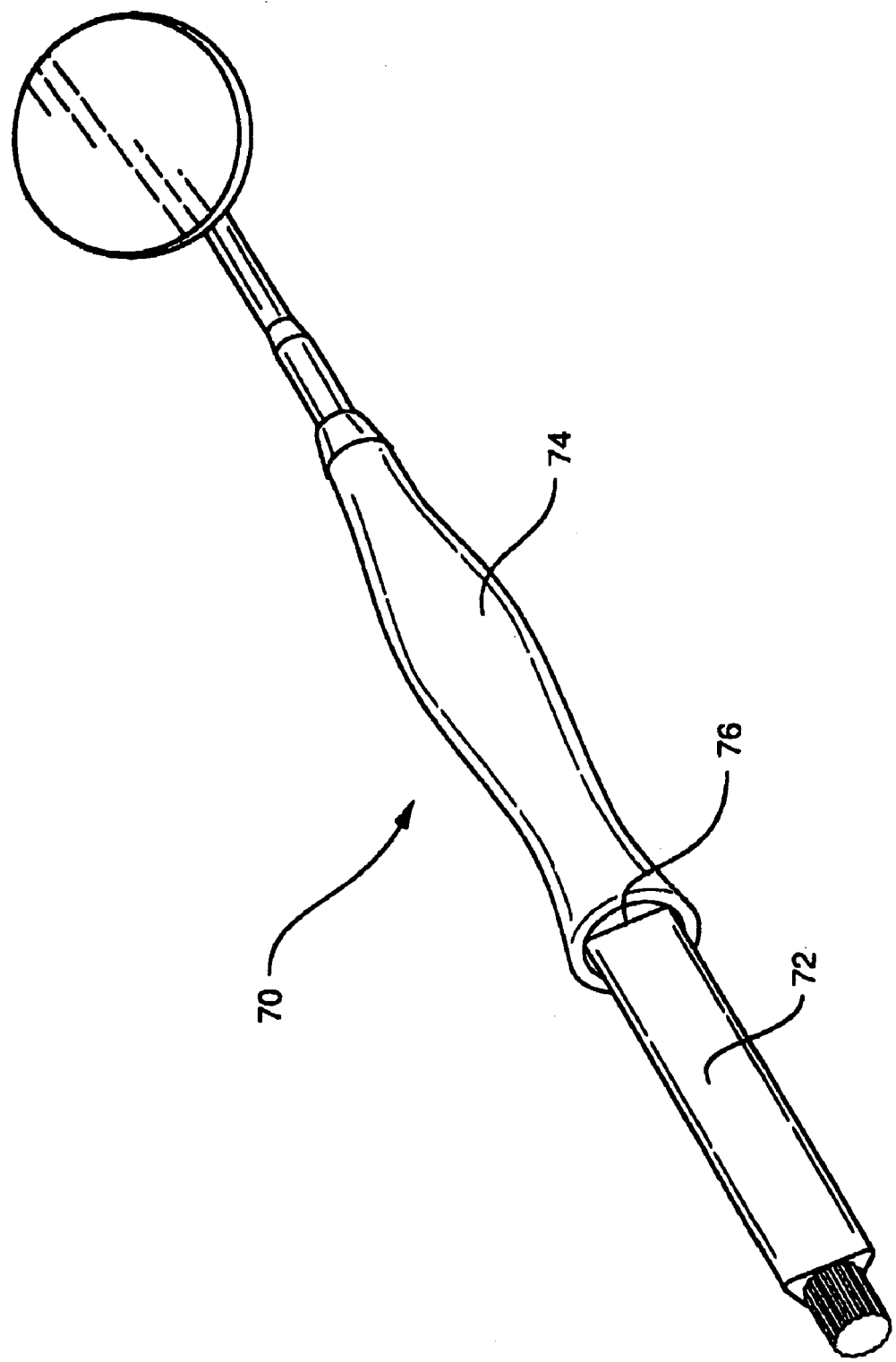
FIG. 6 shows yet another alternative embodiment of the invention.

Embodiment 70, FIG. 6, illustrates alternative shapes of grip portion 74 having end 76, against which triangular-shaped sharpening stone 72 sits. This embodiment also illustrates another alternative feature of the invention to accomplish a guard where the stone meets the grip, which helps prevent the sharp curette tip from sliding onto the grip and cutting the hand. This is accomplished by making end portion 76 of grip 74 larger (i.e., located farther from the instrument shaft) than the matching end portion of the stone. This guard feature can be enhanced by enlarging or flaring end 76 of grip 74 as shown in the drawing, and/or by decreasing the radius of the stone.

Preferred Fabrication Options

Any common means of fabricating stones may be employed; including extruding, plating, molding, and casting. These means allow the forming of stones in many shapes, even complex shapes for the grip such as shown in FIG. 6. Naturally occurring abrasive stones such as Arkansas or India stones may be machined to the finished shapes. Alternatively, industrial stones consisting of binders and abrasives such as aluminas, carbides, and/or nitrides may be used. Also, abrasive "stones" may be formed by plating a metal substrate, typically formed from an aluminum, steel, nickel, or copper alloy, with an abrasive layer. Such layers may include diamonds, aluminas, carbides, and/or nitrides. A part molded with a plastic or elastomer compound impregnated with an abrasive might also be used.

Grips may be cast, injection molded, insert molded, two-shot molded, or liquid injection molded from a variety of rigid or elastomeric resins. Alternatively, grips may be metal, machined from bar stock, cast, forged, or metal injection molded. A variety of surface treatments may be applied to plastic or metal grips to ensure a secure grip when dry or wet. Treatments include finger pockets, knurling, dimpling, fluting, grooving, faceting, ridging, coating, or texturing. A series of grip enhancers may be added to metal or plastic grips, such as elastomeric o-rings or pads. Grips may be shaped for optimal comfort and holding power, minimizing slippage and hygienist fatigue. Different shapes may be optimized for different preferred gripping styles.

Shafts may be made of metal machined from bar stock, forged, cast, or metal-injection-molded. Shafts may also be injection molded from rigid polymers or possibly cast ceramics.

Mirrors may be solid polished metal, or opaque substrates such as plastic or metal with a highly reflective metal coating on the front surface. They may include a protective overcoat such as magnesium fluoride thin film to prevent tarnishing. Alternatively, a diamond-like film may be applied on the mirror surface that would prevent both tarnishing and scratching. Mirrors may be made of a transparent substrate such as plastic, glass, quartz, or sapphire with metalization on the front or back surfaces to provide reflections. A sapphire, back-surface mirror would be highly damage resistant, since the front surface would be virtually scratch-proof, and the reflecting surface would be protected by the mirror holder. This could be a premium offering.

The mirror holders may be made of metal or plastic.

The mirror may be bonded to the mirror holder using an adhesive that will withstand repeated autoclaving. Alternatively, the mirror may be retained by swaging the mirror holder around the mirror's outer edge, or by some other mechanical means.

If both the mirror holder and the shaft are metal, they may be permanently joined by soldering, brazing, welding, pressing, bonding, or threading. Detachable joints using threads or a quick-locking construction using a twist-lock, spring-pin, or ball-lock are also feasible. Detachable joints would permit interchangeability of mirrors and shafts. If both mirrors and shafts are plastic, the mirror holder may be attached to the shaft by a snap interlock, bonding, or threading. Snap or threaded attachments would permit interchangeability of mirrors and shafts. If one part is plastic and the other is metal, bonded, snap or threaded attachments are feasible. If both the mirror and mirror holder are made of metal, they might be combined into a single part formed by casting or forging with secondary polishing and coating operations. If both the mirror and mirror holder are made of plastic, they might be combined into a single part formed by injection molding with secondary mirror coating operations.

If the mirror, mirror holder, and shaft are all made of metal, they might be combined into a single part formed by casting or forging with secondary polishing and coating operations. If all metal, the mirror, mirror holder, shaft, and grip may be combined into a single part a similar way. Other combinations such as a metal-coated glass or plastic mirror attached to a combined mirror holder/shaft and/or grip made of metal are also possible.

The mirror, mirror holder, shaft, and grip may also be combined into a single part made of plastic or metal, with secondary operations to form a reflective surface. This may be configured as a low cost, "disposable" design.

The sharpening stone may be shaped as a grip, and the stone and grip combined into one piece made of the stone material.

The retainer may be attached with a thread, quick-lock, or other tool-less fastening means for easy removal and reattachment. The outside of the retainer may be knurled, fluted, grooved, facetted, or textured to provide good finger grip when turning. The retainer might be eliminated if the stone is bonded in place, or has another retention means such as interference fit, thread, or spring-loaded locking pin. These features may serve as or be combined with anti-rotation features for the stone and/or grip.

Other Embodiments

A sharpening stone of the invention may alternatively be combined with dental instruments/devices other than mirrors of the type that are used in a dental office at the same time as an instrument that needs sharpening, such as a curette. For example, suction application devices and water application devices are sometimes used by hygienists at the same time as a curette. Also, dental instruments other than curettes can require sharpening. The invention thus contemplates the combination of a sharpening stone with a hand-held dental instrument or device that is used in a patient procedure, and the use of this combined instrument or device to sharpen dental instruments, including but not limited to curettes.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A hand-held dental mirror carrying a sharpening stone for a dental instrument, comprising:
   a shaft supporting a mirror;
   a hand grip coupled to the shaft; and
   a sharpening stone coupled to the shaft.

2. The hand-held dental mirror of claim 1 wherein the sharpening stone defines a longitudinal opening through which the shaft passes.

3. The hand-held dental mirror of claim 1, further comprising means for releasably maintaining the stone coupled to the shaft.

4. The hand-held dental mirror of claim 3 wherein the means for releasably maintaining the stone coupled to the shaft comprises a mechanical device at the end of the shaft opposite the mirror.

5. The hand-held dental mirror of claim 4 wherein the mechanical device is releasably coupled to the end of the shaft opposite the mirror.

6. The hand-held dental mirror of claim 1 wherein the sharpening stone defines one end that lies proximate one end of the hand grip.

7. The hand-held dental mirror of claim 6 wherein the one end of the hand grip defines an outer surface that lies farther from the shaft than does the outer surface of the one end of the sharpening stone, to help prevent the dental instrument being sharpened from sliding past the stone onto the grip.

8. The hand-held dental mirror of claim 1 wherein the hand grip and the sharpening stone are both releasably coupled to the shaft.

* * * * *